(12) United States Patent
Gross et al.

(10) Patent No.: US 9,597,179 B2
(45) Date of Patent: Mar. 21, 2017

(54) SINUS STENT

(71) Applicant: RAINBOW MEDICAL LTD., Herzliya (IL)

(72) Inventors: Yossi Gross, Moshav Mazor (IL); Hadar Better, Tel Aviv (IL); Gideon Fostick, Givat Shmuel (IL); Ilan Uchitel, Kefar Saba (IL)

(73) Assignee: RAINBOW MEDICAL LTD., Herzliya (IL)

( * ) Notice: Subject to any disclaimer, the term of this patent is extended or adjusted under 35 U.S.C. 154(b) by 0 days.

(21) Appl. No.: 14/636,886

(22) Filed: Mar. 3, 2015

(65) Prior Publication Data
US 2015/0173894 A1   Jun. 25, 2015

Related U.S. Application Data

(62) Division of application No. 13/189,896, filed on Jul. 25, 2011, now Pat. No. 8,998,985.

(51) Int. Cl.
| | | |
|---|---|---|
| *A61F 2/18* | (2006.01) | |
| *A61F 11/00* | (2006.01) | |
| *A61B 18/14* | (2006.01) | |
| *A61F 2/82* | (2013.01) | |
| *A61F 2/958* | (2013.01) | |
| *A61B 18/00* | (2006.01) | |

(52) U.S. Cl.
CPC ............ *A61F 2/186* (2013.01); *A61B 18/14* (2013.01); *A61F 2/82* (2013.01); *A61F 2/958* (2013.01); *A61F 11/00* (2013.01); *A61F 11/002* (2013.01); *A61B 2018/00327* (2013.01); *A61B 2018/00595* (2013.01); *A61F 2210/0004* (2013.01)

(58) Field of Classification Search
CPC .................................. A61F 2/18; A61F 2/186
See application file for complete search history.

(56) References Cited

U.S. PATENT DOCUMENTS

| | | |
|---|---|---|
| 4,737,141 A | 4/1988 | Spits |
| 5,139,502 A | 8/1992 | Berg et al. |
| 5,246,455 A | 9/1993 | Shikani |
| 5,421,727 A | 6/1995 | Stevens et al. |
| 5,897,521 A | 4/1999 | Lavigne |
| 6,251,121 B1 | 6/2001 | Saadat |
| 6,645,227 B2 | 11/2003 | Fallin et al. |
| 6,719,781 B1 | 4/2004 | Kim |
| 6,988,986 B2 | 1/2006 | Gross |
| 7,062,317 B2 | 6/2006 | Avrahami et al. |

(Continued)

FOREIGN PATENT DOCUMENTS

| | | |
|---|---|---|
| WO | WO2004010858 A2 | 2/2004 |
| WO | WO2004066903 A2 | 8/2004 |

OTHER PUBLICATIONS

An Office Action dated Aug. 25, 2014 which issued during the prosecution of U.S. Appl. No. 13/189,896.

(Continued)

*Primary Examiner* — Jason-Dennis Stewart
(74) *Attorney, Agent, or Firm* — Sughrue Mion, PLLC (57) ABSTRACT

Apparatus and methods are described, including a method for treating a paranasal sinus of a subject. The method includes forming an artificial hole in a wall of the paranasal sinus, and, via the artificial hole, opening a natural ostium of the paranasal sinus. Other applications are also described.

9 Claims, 7 Drawing Sheets

(56) References Cited

U.S. PATENT DOCUMENTS

| | | |
|---|---|---|
| 7,087,011 B2 | 8/2006 | Cabiri et al. |
| 7,410,480 B2 | 8/2008 | Muni et al. |
| 7,455,677 B2 | 11/2008 | Vargas et al. |
| 7,462,162 B2 | 12/2008 | Phan et al. |
| 7,520,876 B2 | 4/2009 | Ressemann et al. |
| 7,544,160 B2 | 6/2009 | Gross |
| 7,635,345 B2 | 12/2009 | Gross et al. |
| 7,635,346 B2 | 12/2009 | Cabiri et al. |
| 7,678,099 B2 | 3/2010 | Ressemann et al. |
| 7,753,930 B2 | 7/2010 | Becker |
| 7,833,176 B2 | 11/2010 | Gross et al. |
| 7,934,929 B2 | 5/2011 | Better et al. |
| 7,947,013 B2 | 5/2011 | Cabiri et al. |
| 8,114,062 B2 | 2/2012 | Muni et al. |
| 8,182,432 B2 | 5/2012 | Kim et al. |
| 8,388,343 B2 | 3/2013 | Better et al. |
| 8,414,473 B2 | 4/2013 | Jenkins et al. |
| 8,419,678 B2 | 4/2013 | Cabiri et al. |
| 8,439,687 B1 | 5/2013 | Morriss et al. |
| 8,496,580 B2 | 7/2013 | Dotan et al. |
| 8,556,627 B2 | 10/2013 | Better et al. |
| 8,602,974 B2 | 12/2013 | Goldwasser et al. |
| 8,696,354 B2 | 4/2014 | Fostick et al. |
| 8,702,423 B2 | 4/2014 | Better et al. |
| 8,702,620 B2 | 4/2014 | Gefen et al. |
| 8,702,626 B1 | 4/2014 | Kim et al. |
| 8,721,334 B2 | 5/2014 | Better et al. |
| 8,747,389 B2 | 6/2014 | Goldfarb et al. |
| 8,764,729 B2 | 7/2014 | Muni et al. |
| 8,876,730 B2 | 11/2014 | Cabiri et al. |
| 8,939,895 B2 | 1/2015 | Simchony et al. |
| 8,998,985 B2 | 4/2015 | Gross et al. |
| 2004/0102681 A1 | 5/2004 | Gross |
| 2005/0036059 A1 | 2/2005 | Goldwasser |
| 2005/0038318 A1 | 2/2005 | Goldwasser |
| 2005/0038319 A1 | 2/2005 | Goldwasser et al. |
| 2005/0038335 A1 | 2/2005 | Gross et al. |
| 2005/0154278 A1 | 7/2005 | Cabiri et al. |
| 2005/0154355 A1 | 7/2005 | Gross et al. |
| 2005/0197531 A1 | 9/2005 | Cabiri et al. |
| 2005/0240147 A1* | 10/2005 | Makower .......... A61B 17/24 604/96.01 |
| 2005/0267478 A1 | 12/2005 | Corradi et al. |
| 2006/0106361 A1 | 5/2006 | Muni et al. |
| 2006/0201351 A1 | 9/2006 | Gross et al. |
| 2006/0276871 A1 | 12/2006 | Lamson et al. |
| 2007/0233005 A1 | 10/2007 | McMichael et al. |
| 2008/0097292 A1 | 4/2008 | Cabiri et al. |
| 2008/0161645 A1 | 7/2008 | Goldwasser et al. |
| 2008/0172010 A1 | 7/2008 | Degtiar et al. |
| 2008/0195041 A1 | 8/2008 | Goldfarb et al. |
| 2008/0215083 A1 | 9/2008 | Becker |
| 2008/0243140 A1 | 10/2008 | Gopferich et al. |
| 2008/0243151 A1 | 10/2008 | Binmoeller et al. |
| 2008/0319424 A1 | 12/2008 | Muni et al. |
| 2009/0030274 A1 | 1/2009 | Goldfarb et al. |
| 2009/0036968 A1* | 2/2009 | Hepworth .......... A61F 2/186 623/1.11 |
| 2009/0082629 A1 | 3/2009 | Dotan et al. |
| 2009/0182197 A1 | 7/2009 | Goldwasser et al. |
| 2009/0198216 A1 | 8/2009 | Muni et al. |
| 2009/0216196 A1 | 8/2009 | Drontle et al. |
| 2009/0275857 A1 | 11/2009 | Cabiri et al. |
| 2009/0312745 A1 | 12/2009 | Goldfarb et al. |
| 2010/0030031 A1 | 2/2010 | Goldfarb et al. |
| 2010/0081112 A1 | 4/2010 | Better et al. |
| 2010/0099946 A1 | 4/2010 | Jenkins et al. |
| 2010/0121308 A1 | 5/2010 | Muni et al. |
| 2010/0272318 A1 | 10/2010 | Cabiri et al. |
| 2011/0004057 A1 | 1/2011 | Goldfarb et al. |
| 2011/0004194 A1 | 1/2011 | Eaton et al. |
| 2011/0029007 A1 | 2/2011 | Arcand et al. |
| 2011/0092765 A1 | 4/2011 | Goldwasser et al. |
| 2011/0112512 A1 | 5/2011 | Muni et al. |
| 2011/0160536 A1 | 6/2011 | Blum |
| 2011/0160740 A1 | 6/2011 | Makower et al. |
| 2011/0295146 A1 | 12/2011 | Gefen et al. |
| 2012/0136207 A1 | 5/2012 | Goldfarb et al. |
| 2012/0227457 A1 | 9/2012 | Kim et al. |
| 2012/0265094 A1 | 10/2012 | Goldfarb et al. |
| 2012/0283514 A1 | 11/2012 | Simchony et al. |
| 2013/0006055 A1 | 1/2013 | Goldfarb et al. |
| 2013/0149669 A1 | 6/2013 | Fostick et al. |
| 2013/0165873 A1 | 6/2013 | Morriss et al. |
| 2013/0261388 A1 | 10/2013 | Jenkins et al. |
| 2013/0274600 A1 | 10/2013 | Jenkins et al. |
| 2013/0276794 A1 | 10/2013 | Morriss |
| 2014/0074065 A1 | 3/2014 | Muni et al. |
| 2014/0074140 A1 | 3/2014 | Johnson et al. |
| 2014/0074141 A1 | 3/2014 | Johnson et al. |
| 2014/0107427 A1 | 4/2014 | Chow et al. |
| 2014/0147809 A1 | 5/2014 | Uchitel et al. |
| 2014/0200444 A1 | 7/2014 | Kim et al. |
| 2014/0261545 A1 | 9/2014 | Jenkins et al. |
| 2014/0261579 A1 | 9/2014 | Jenkins et al. |
| 2014/0275775 A1 | 9/2014 | Jones et al. |
| 2014/0275804 A1 | 9/2014 | Kesten et al. |
| 2014/0276328 A1 | 9/2014 | Kesten et al. |
| 2014/0276625 A1 | 9/2014 | Jenkins et al. |
| 2014/0276626 A1 | 9/2014 | Jenkins et al. |
| 2014/0276627 A1 | 9/2014 | Jenkins et al. |
| 2014/0276654 A1 | 9/2014 | Jenkins |
| 2014/0277039 A1 | 9/2014 | Liberatore et al. |
| 2014/0277043 A1 | 9/2014 | Jenkins et al. |
| 2014/0277071 A1 | 9/2014 | Wu et al. |
| 2014/0336575 A1 | 11/2014 | Muni et al. |
| 2014/0336693 A1 | 11/2014 | Goldfarb et al. |
| 2014/0343498 A1 | 11/2014 | Morriss et al. |
| 2014/0350465 A1 | 11/2014 | Muni et al. |
| 2015/0005805 A1 | 1/2015 | Kesten et al. |

OTHER PUBLICATIONS http://www.google.co.il/search?q=punch+drill+bitbone&espvd=2 &biw=911&bih=425&source=lnms&tbm=isch&sa=X &ei=blvcVJj_HIP5UrvrgJgF&ved=0CAY; downloaded Feb. 12, 2015.

* cited by examiner

SINUS STENT

CROSS REFERENCE TO RELATED APPLICATIONS

The present application is a divisional of U.S. application Ser. No. 13/189,896 to Gross et al., entitled "Sinus Stent," filed Jul. 25, 2011, which published as US 2013/0030545 (now U.S Pat. No. 8,998,985) and is incorporated herein by reference.

FIELD OF THE INVENTION

Applications of the present invention relate generally to treatment of sinus disorders, and specifically to implantable medical devices for treating sinus disorders.

BACKGROUND

Sinusitis is a common condition, characterized by symptoms such as nasal discharge, facial and ear pressure and pain, headache, loss of smell, fever, cough and fatigue. Physiological clearing of paranasal sinuses is via mucociliary transport through the ostia (natural sinus openings into a nasal cavity). Disruption of this function, often associated with partial blockage of an ostium, allows stagnation of mucous secretions and alteration of pH and other physiologic parameters, making the sinus conditions more favorable to microbiological growth and, therefore, susceptible to sinusitis. Treatment of chronic sinusitis typically includes antibiotics, steroids, decongestants and, in some cases, surgical procedures such as lavage.

SUMMARY OF THE INVENTION

In some applications of the invention, a hole-forming member is coupled to an implant. The hole-forming member forms a hole in a bone wall of a sinus, and facilitates implantation of the implant in the formed hole. The apparatus disclosed according to these applications of the invention allows hole-forming and implantation to be performed conveniently. Several versions of the implant are described, each being shaped to define a lumen which, following implantation, provides communication between the sinus and the nasal cavity of the subject. This allows drainage from the sinus, access to the sinus by medical instruments, and the possibility of administering therapeutic substances to the sinus. Typically, the implant is left in place for at least several days, allowing repeated access to the sinus without the need for repeated hole-forming.

In some applications of the invention, the paranasal sinus implant is self-tapping. In these applications, no separate hole-forming member is used.

In some applications of the invention, a stent is implanted in a natural sinus ostium in order to treat sinusitis. The stent is typically implanted using a balloon catheter, which is inserted into the sinus ostium, typically via an artificial hole in the bone wall of the sinus. For example, the insertion of the stent into the sinus ostium is performed following implantation of an implant with a lumen, as described above. The stent is positioned in the ostium while in a compressed configuration on the balloon of the balloon catheter. Inflation of the balloon expands the stent, which remains expanded after the balloon is deflated and removed, thereby holding the ostium in an open configuration. Alternatively, the stent may be delivered to the ostium in a contracted form, such as within a sheath, expanding upon removal of the sheath.

In some applications of the invention, a rivet implant is implanted in an anatomical wall or other tissue of a subject. The rivet implant typically acts as a blind rivet. Deformation of a distal portion of the implant secures the implant in the tissue.

In some applications of the invention, a cauterizing hole-forming member is used to form the hole in the wall of the sinus. The wall of the sinus includes a bone layer and membranous layers. In these applications of the invention, the hole-forming member comprises a drill bit slidably coupled to at least one radio frequency (RF) electrode, the drill bit being configured to penetrate the bone layer and the RF electrodes being configured to penetrate and cauterize the membranous layers. Axially sliding the drill bit and RF electrodes with respect to each other allows penetration of the appropriate layer with the respective appropriate component of the hole-forming member.

There is therefore provided, in accordance with an application of the present invention, paranasal sinus apparatus including:
  a hole-forming member configured to form a hole through
    a wall of a paranasal sinus of a subject; and
  an implant having a proximal end, a distal end, and shaped
    to define a lumen, the implant:
    being couplable to the hole-forming member,
    being securable to the wall and extendable through the
      hole, such that the proximal end is disposed external
      to the paranasal sinus and the distal end is disposed
      within the paranasal sinus, and
    including a biodegradable material.

In an application, at least part of the hole-forming member is disposable within the lumen of the implant, and the implant is slidably movable over at least part of the hole-forming member.

In an application, the apparatus includes a tube, disposable within the lumen of the implant, and the implant is slidably movable over the tube.

In an application, at least part of the implant is disposable within a void defined by the hole-forming member, and the implant is slidably movable through at least part of the hole-forming member.

In an application, the apparatus includes a tube, disposable within the lumen of the implant, and the hole-forming member is disposable within the tube, and the hole-forming member is slidably movable within the tube.

In an application, the hole-forming member is configured to form the hole in a wall that is a part of a maxilla of the subject that divides a nasal cavity of the subject and a maxillary sinus of the subject, and the implant has a length appropriate to extend through the hole in the bone wall.

In an application, the hole-forming member includes a drill bit.

In an application, the hole-forming member includes a piercing device.

In an application, the hole-forming member includes an ultrasonic drill.

In an application, the hole-forming member includes a water jet cutter.

In an application, the hole-forming member includes a laser cutter.

In an application, the implant is securable to the wall in an irreversible manner.

In an application, the implant is securable to the wall in a reversible manner.

In an application, the hole-forming member is coupled to the implant.

In an application, the hole-forming member is decouplable from the implant.

In an application, the implant is shaped to define the lumen, the lumen having a diameter sufficient to allow flow of liquid secretions from the distal end to the proximal end of the implant.

In an application, the implant is shaped to define the lumen, the lumen having a diameter of between 0.5 mm and 15 mm (e.g., at least 0.5 mm and/or less than 2 mm; at least 2 mm and/or less than 6 mm; or at least 6 mm and/or less than 15 mm).

In an application, the implant has a length of between 1 mm and 30 mm (e.g., at least 1 mm and/or less than 4 mm; at least 4 mm and/or less than 12 mm; or at least 12 mm and/or less than 30 mm).

In an application, the apparatus includes a medical instrument, passable through the lumen of the implant.

In an application, the apparatus includes a control unit and a radio frequency electrode, wherein:
the hole-forming member is couplable to the radio frequency electrode,
the radio frequency electrode is couplable to the control unit, and
the control unit is configurable to drive a radio frequency current through the electrode.

In an application, the control unit is configured to configure the current to reduce bleeding from tissue in a vicinity of the hole formed by the hole-forming member.

In an application:
the apparatus further includes a control unit,
the hole-forming member includes a radio frequency electrode, couplable to the control unit, and
the control unit is configured to drive a radio frequency current through the electrode.

In an application, the control unit is configured to configure the current to form the hole through at least a part of the wall of the paranasal sinus of the subject.

In an application, the hole-forming member further includes a drill bit, slidably coupled to the radio frequency electrode.

In an application, the apparatus further includes a cooling element, configured to apply cooling in conjunction with forming the hole by the hole-forming member.

In an application, the cooling element is configured to apply the cooling at least prior to the forming of the hole by the hole-forming member.

In an application, the cooling element is configured to apply the cooling to a site of forming of the hole by the hole-forming member.

In an application, the cooling element includes a compressed gas.

In an application, the cooling element includes a cooled liquid.

In an application, the cooling element is configured to apply the cooling to the hole-forming member.

In an application, the cooling element is coupled to the hole-forming member.

There is further provided, in accordance with an application of the present invention, paranasal sinus apparatus including:
an implant, the implant:
having a length of between 1 mm and 30 mm (e.g., at least 1 mm and/or less than 4 mm; at least 4 mm and/or less than 12 mm; or at least 12 mm and/or less than 30 mm),
being shaped to define a lumen, and the lumen has a diameter of between 0.5 mm and 15 mm (e.g., at least 0.5 mm and/or less than 2 mm; at least 2 mm and/or less than 6 mm; or at least 6 mm and/or less than 15 mm),
having a proximal portion, a middle portion and a distal portion, each portion has an external diameter, and the external diameter of the middle portion is between 1 mm and 20 mm (e.g., at least 1 mm and/or less than 4 mm; at least 4 mm and/or less than 10 mm; and/or at least 10 mm and/or less than 20 mm); and
a hole-forming member, couplable to the implant and configured to form a hole in a wall of a paranasal sinus of a subject.

In an application, at least part of the hole-forming member is disposable within the lumen of the implant, and the implant is slidably movable over at least part of the hole-forming member.

In an application, the apparatus includes a tube, disposable within the lumen of the implant, and the implant is slidably movable over the tube.

In an application, the hole-forming member is coupled to the implant.

In an application, the hole-forming member is decouplable from the implant.

In an application, the implant is securable to the wall of the paranasal sinus of a subject.

In an application, the implant is securable to a wall that is a part of a maxilla of the subject that divides a nasal cavity of the subject and a maxillary sinus of the subject.

In an application, the implant is securable to the wall in an irreversible manner.

In an application, the implant is securable to the wall in a reversible manner.

In an application, the implant includes a biodegradable material.

In an application, the implant is entirely biodegradable.

In an application, the apparatus includes a tube, disposable within the lumen of the implant, the hole-forming member is disposable within the tube, and the hole-forming member is slidably movable within the tube.

In an application, the hole-forming member includes a drill bit.

In an application, the hole-forming member includes a piercing device.

In an application, the hole-forming member includes an ultrasonic drill.

In an application, the hole-forming member includes a water jet cutter.

In an application, the hole-forming member includes a laser cutter.

In an application, the apparatus includes a control unit and a radio frequency electrode, wherein:
the hole-forming member is couplable to the radio frequency electrode,
the radio frequency electrode is couplable to the control unit, and
the control unit is configurable to drive a radio frequency current through the electrode.

In an application, the control unit is configured to configure the current to reduce bleeding from tissue in a vicinity of the hole formed by the hole-forming member.

In an application:
the apparatus further includes a control unit,
the hole-forming member includes a radio frequency electrode, couplable to the control unit, and
the control unit is configured to drive a radio frequency current through the electrode.

In an application, the control unit is configured to configure the current to form the hole through at least part of the wall of the paranasal sinus of the subject.

In an application, the hole-forming member further includes a drill bit and

In an application, the apparatus further includes a cooling element, the cooling element being configured to apply cooling in conjunction with formation of the hole by the hole-forming member.

In an application, the cooling element is configured to apply the cooling at least prior to formation of the hole by the hole-forming member.

In an application, the cooling element is configured to apply the cooling to a site of formation of the hole by the hole-forming member.

In an application, the cooling element includes a compressed gas.

In an application, the cooling element includes a cooled liquid.

In an application, the cooling element is configured to apply the cooling to the hole-forming member.

In an application, the cooling element is coupled to the hole-forming member.

There is further provided, in accordance with an application of the present invention, paranasal sinus apparatus including:
 a blind rivet implant, shaped to define a lumen and having a proximal end and a distal end, the implant:
  having a length appropriate to extend through a hole in a wall of a paranasal sinus of a subject so that the proximal end is disposed external to the paranasal sinus and the distal end is disposed within the paranasal sinus,
  being securable to the wall, and
  including at a distal region of the implant a buck-tail, being deformable from a first shape to a second shape, the geometry of the first shape permitting passage of the distal region through the hole in the wall of the paranasal sinus, and the geometry of the second shape preventing such passage; and
 an applicator, shaped so that a distal region of the applicator is disposable within the lumen of the implant, the applicator being removable from the implant.

In an application, the apparatus includes a restraint disposable within the lumen of the implant, wherein:
 the applicator is couplable to the restraint,
 the first shape of the buck-tail is a constrained shape and the second shape of the buck-tail is an unconstrained shape,
 the restraint is configured to retain the buck-tail in the first shape when the restraint is disposed within the lumen of the implant, and
 the buck-tail is configured such that it moves from the first shape to the second shape upon removal of the restraint from the implant.

In an application:
 the first and second shapes of the buck-tail are unconstrained shapes, and
 the buck-tail and the distal region of the applicator are configured such that a force applied to the buck-tail by the distal region of the applicator deforms the buck-tail from the first shape to the second shape.

In an application, the length appropriate to extend through the hole in the wall of the paranasal sinus of the subject is a length appropriate to extend through an artificial hole in a wall that is a part of a maxilla of the subject that divides a nasal cavity of the subject and a maxillary sinus of the subject.

In an application, the implant is securable to the wall of the subject in an irreversible manner.

In an application, the implant is securable to the wall of the subject in a reversible manner.

In an application, the lumen of the implant has a diameter sufficient to allow flow of liquid secretions from the distal end to the proximal end of the implant.

In an application, the lumen of the implant has a diameter of between 0.5 mm and 15 mm.

In an application, the implant has a length of between 1 mm and 30 mm.

In an application, the implant includes a biodegradable material.

In an application, the implant is entirely biodegradable.

In an application, the apparatus includes a medical instrument, passable through the lumen of the implant.

In an application, the medical instrument includes at least one instrument selected from the group consisting of: an endoscope, an aspirator, and a syringe.

There is further provided, in accordance with an application of the present invention, paranasal sinus apparatus including:
 An implant, implantable in a wall of a paranasal sinus of a subject, and shaped to define a lumen;
  a catheter slidable through the lumen of the implant;
  a balloon, couplable to a distal portion of the catheter; and
  an expandable stent, slidable through the lumen of the implant, shaped to define a lumen, and configured such that it may be expanded from a first shape to an expanded shape by an applied force,
  the balloon being inflatable via the catheter, and disposable within the lumen of the expandable stent such that inflation of the balloon expands the expandable stent, and
  the expandable stent being maintainable in the expanded shape when the balloon is deflated.

In an application, the balloon is coupled to the distal portion of the catheter.

In an application, the stent includes a biodegradable material.

In an application, the apparatus further includes a guidewire, and the catheter is advanceable over the guidewire.

There is further provided, in accordance with an application of the present invention, a method for implanting an implant in a wall of a paranasal sinus of a subject, the implant being shaped to define a lumen, the method including:
 coupling a hole-forming member to a portion of a body of the subject;
 forming a hole at a site on the wall of the paranasal sinus using the hole-forming member, while the hole-forming member is coupled to the implant; and
 while the hole-forming member is coupled to the portion of the body of the subject, inserting at least part of the implant into the hole.

In an application, at least part of the hole-forming member is disposable within the lumen of the implant and the implant is slidably couplable to the hole-forming member, and inserting at least part of the implant into the hole includes sliding the implant along at least part of the hole-forming member.

In an application, at least part of the implant is disposable within a void defined by the hole-forming member, and inserting at least part of the implant into the hole includes sliding the implant through at least part of the hole-forming member.

In an application, forming the hole at the site on the wall of the paranasal sinus includes forming a hole at a site on a wall that is between a nasal cavity and a maxillary sinus of the subject.

In an application, forming the hole at the site on the wall of the paranasal sinus includes forming the hole at a site that is inferior to an inferior turbinate of a lateral nasal wall.

In an application, the implant has a proximal end and a distal end, and inserting at least part of the implant into the hole includes inserting the implant such that the proximal end is disposed external to the paranasal sinus and the distal end is disposed within the paranasal sinus.

In an application, the method includes facilitating drainage of material from the sinus via the lumen of the implant.

In an application, the method includes administering a substance to the sinus via the lumen of the implant.

In an application, inserting at least part of the implant into the hole includes inserting at least part of an implant that includes a biodegradable material into the hole.

In an application, inserting at least part of the implant into the hole includes advancing the hole-forming member distally.

In an application, inserting at least part of the implant into the hole includes pushing the implant using the hole-forming member.

In an application, the method further includes applying cooling in conjunction with forming the hole using the hole-forming member.

In an application, applying cooling includes applying cooling to the hole-forming member.

In an application, applying cooling includes applying cooling at least prior to the forming of the hole using the hole-forming member.

In an application, applying cooling includes applying cooling to the site on the wall.

In an application, applying cooling includes applying cooling at least prior to the forming of the hole using the hole-forming member.

In an application, applying cooling includes expanding a compressed gas.

In an application, applying cooling includes applying a liquid.

There is further provided, in accordance with an application of the present invention, a method for implanting an implant in a subject, the method including:

inserting the implant through a hole in a tissue of the subject, the implant being configured to act as a blind rivet and including a buck-tail at a distal region of the blind rivet; and deforming the buck-tail from a first shape that allows passage of the buck-tail through the hole into a second shape that does not allow passage of the buck-tail through the hole.

In an application, deforming the buck-tail includes applying a deforming force.

In an application, deforming the buck-tail includes removing a restraint.

In an application, the implant is shaped to define a lumen, and the method further includes facilitating drainage of the sinus via the lumen of the implant.

In an application, the implant is shaped to define a lumen, and the method further includes administering a substance to the sinus via the lumen of the implant.

In an application, inserting the implant through the hole includes inserting the implant through a hole in an anatomical wall of the subject.

In an application, inserting the implant through the hole in the anatomical wall of the subject includes inserting the implant through a hole in a wall of a hollow organ of the subject.

In an application, inserting the implant through the hole in the anatomical wall includes inserting the implant through a hole in a wall of a maxillary sinus of the subject.

In an application, the method further includes forming the hole.

In an application, forming the hole includes forming the hole with the implant.

There is further provided, in accordance with an application of the present invention, a method for implanting a stent in a natural ostium of a paranasal sinus of a subject, the method including:

inserting the stent into the paranasal sinus via an artificial hole in a wall of the sinus, placing the stent in the ostium from inside of the sinus; and securing the stent in the ostium by expanding the stent.

In an application, inserting the stent into the paranasal sinus includes inserting the stent into a maxillary sinus of the subject.

In an application, inserting the stent into the sinus via the artificial hole includes inserting the stent into the sinus via a lumen of an implant implanted in the hole.

There is further provided, in accordance with an application of the present invention, a method for forming a hole in a multilayered tissue of a subject, the method including:

forming a hole in one layer of the tissue of the subject with a drill bit, the drill bit being slidably coupled to a radio frequency electrode;

forming a hole in another layer of the tissue of the subject with the radio frequency electrode; and axially sliding the radio frequency electrode with respect to the drill bit.

In an application, the multilayered tissue of the subject includes a bone layer and at least one membrane layer, and forming the hole in the one layer includes forming a hole in the bone layer, and wherein forming the hole in the other layer includes forming a hole in the membrane layer.

DETAILED DESCRIPTION OF EMBODIMENTS

Figure 1A:
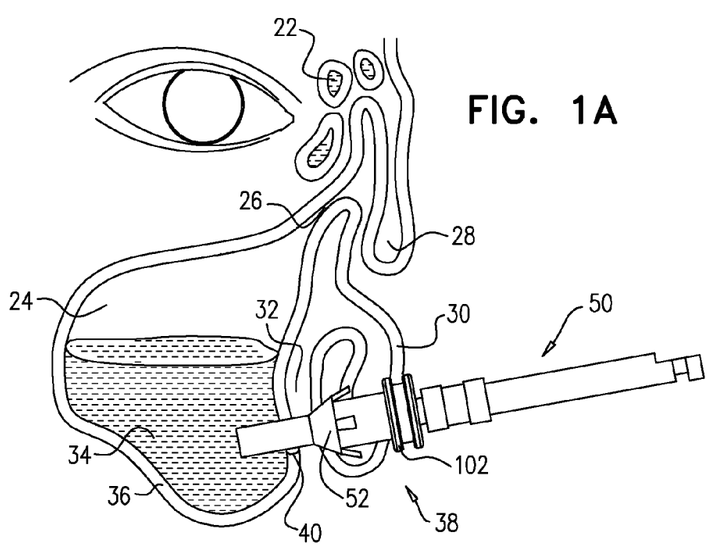
FIGS. 1A-B are schematic illustrations of apparatus for forming a hole in a wall of a paranasal sinus and implanting a paranasal sinus implant in the hole, in accordance with respective applications of the invention.

Reference is made to FIG. 1A, which illustrates a therapeutic approach, in accordance with one application of the invention. The figure includes an anatomical representation showing paranasal sinuses located within the head of a subject. Between the eyes are ethmoid sinuses 22. Located behind the cheek are maxillary sinuses 24. Within nasal cavity 38 are middle turbinate 28 and inferior turbinate 30. Separating nasal cavity 38 from maxillary sinus 24 is bone wall 32, which is part of the maxilla bone of the skull. The sinus cavities have a mucosal lining 36 over the bone. The figure illustrates pus 34 present in sinuses due to sinusitis. The maxillary sinus ostia 26 are located high on the wall of the sinus cavity. Therefore drainage of the sinuses is not aided by gravity, making the maxillary sinuses particularly susceptible to sinusitis.

A hole-forming member 50 is inserted through nasal cavity 38 at an angle such that it contacts bone wall 32, and is operated to form a hole 40 in bone wall 32, below the inferior turbinate. Hole 40 thereby becomes an opening into maxillary sinus 24. For some applications, hole-forming member 50 itself enters bone wall 32. As hole-forming member 50 is advanced into hole 40, an implant 52 is pushed into the hole, optionally accompanied by sliding of the implant along the hole-forming member, typically until a shoulder 102 of the implant meets the surface of the bone wall. For other applications, hole-forming member 50 does not itself penetrate the bone wall. In such a case, implant 52 is typically inserted into hole 40 by sliding it along hole-forming member 50.

Figure 1B:
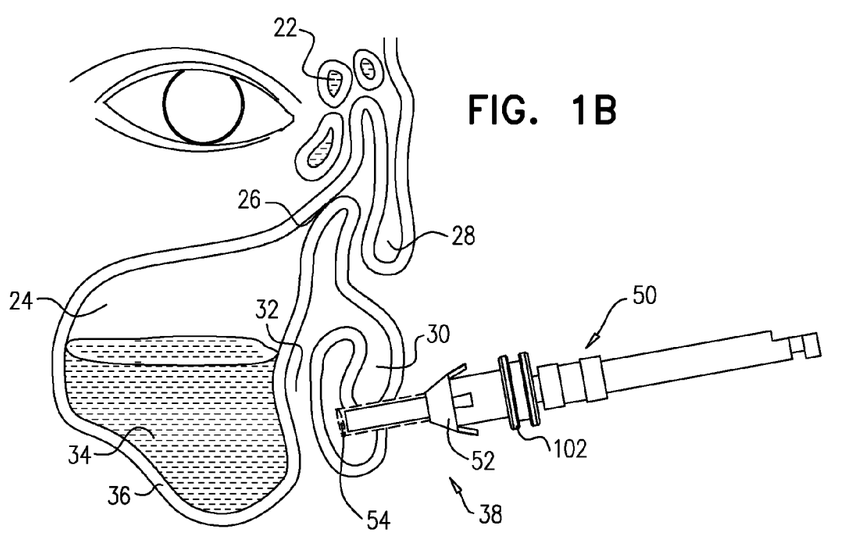

Reference is made to FIG. 1B, which illustrates an alternative application of the invention. Hole-forming member 50 is disposed within a sleeve 54 which, itself, fits within the lumen of implant 52. Sleeve 54 is placed in contact with bone wall 32; this contact is maintained throughout some or all of the procedure. For example, sleeve 54 may be pressed against the bone, and may have anchors (e.g., sharp protrusions) which enter the bone. Hole-forming member 50 is extended through sleeve 54 and forms hole 40. Alternatively, hole-forming member 50 is disposed at a fixed position within sleeve 54. (Examples of versions of hole-forming member 50 are included in FIGS. 5A-E.)

Figure 2:
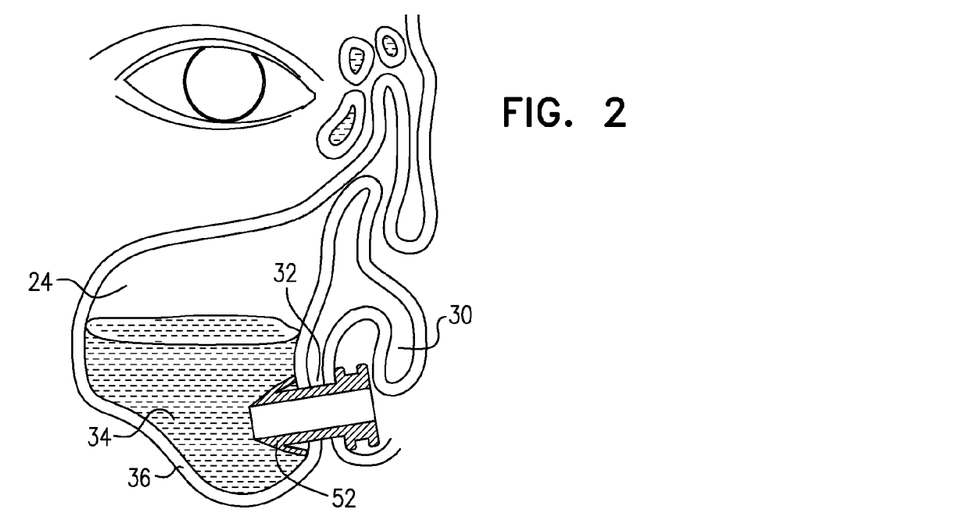
FIG. 2 is a schematic illustration of a paranasal sinus implant, secured in the hole in the wall of the paranasal sinus, in accordance with an application of the invention.

FIG. 2 illustrates implant 52 secured in bone wall 32 of maxillary sinus 24, following the removal of hole-forming member 50, in accordance with an application of the present invention. Implant 52 is shaped to define a lumen. A distal end of the implant is disposed in maxillary sinus 24, and a proximal end is disposed in nasal cavity 38, thus providing communication between the sinus and the nasal cavity. An application of the invention is the implantation of implant 52 in order to facilitate passage of secretions and gaseous exchange between the sinus and nasal passage. Such passage may be passive, such as by circulation of a gas, or by gravity-driven drainage, or the passage may be actively induced by a medical practitioner, using a medical device, for example as described with reference to FIG. 3.

In some applications of the invention, implantation of implant 52 is performed in combination with other procedures such as functional endoscopic sinus surgery (FESS), orthognathic surgery, and treatment of facial fractures and nasal polyps. Implant 52 may be used to facilitate the procedure (e.g., by improving access), or to facilitate pre- or post-procedure treatments, such as the application of therapeutic substances.

In some applications of the invention, hole-forming member 50 (e.g., drill 150) is hollow, or shaped to define a void. Implant 52 is typically disposed within the hollow or void while hole 40 is formed by the hole-forming member. Implant 52 is then moved out of the void, distally, typically by sliding the implant through hole-forming member 50. Implant 52, or a part thereof (e.g., wings 104, described with reference to FIG. 5A) expands within hole 40, securing the implant in place.

In some applications of the invention, implant 52 is self-tapping, comprising a self-tapping screw-thread. In these applications of the invention, no independent hole-forming member is required. Rather, implant 52 is pushed against bone wall 32 and rotated such that it cuts into, and becomes implanted in, the bone wall.

Figure 3:
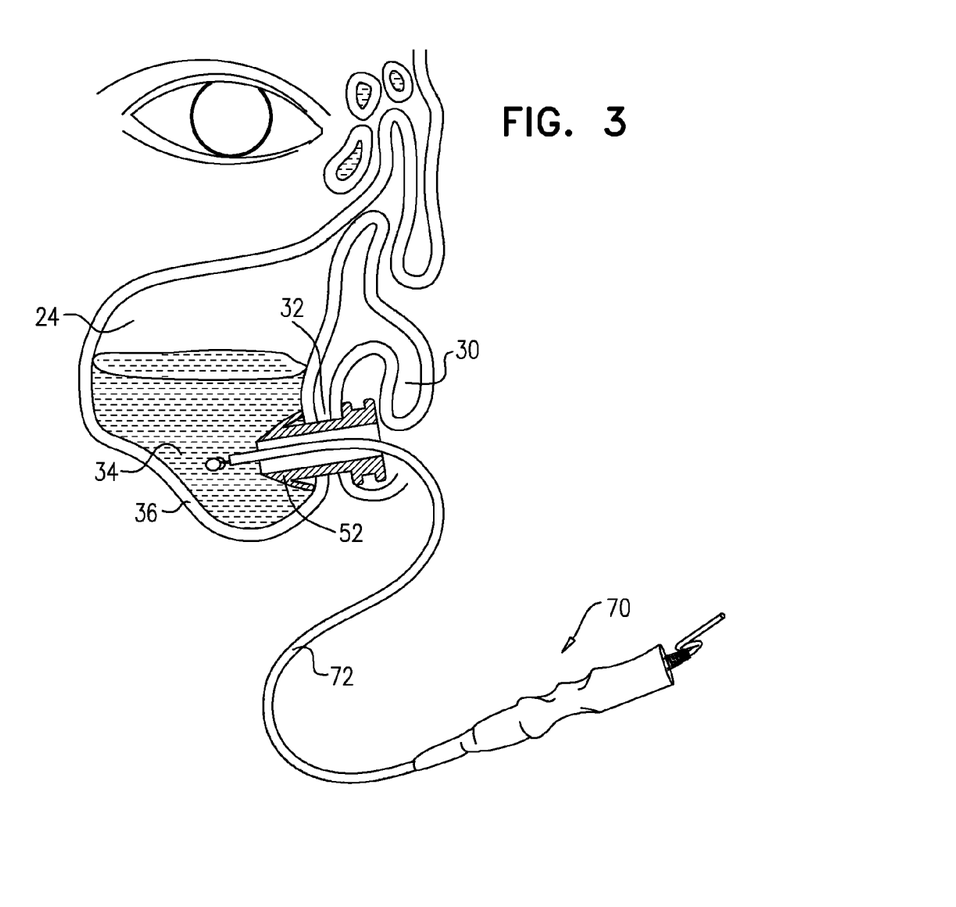
FIG. 3 is a schematic illustration of access of a medical instrument to the paranasal sinus via the paranasal sinus implant, in accordance with an application of the invention.

Reference is now made to FIG. 3, which is a schematic illustration of a medical instrument 70 being inserted through the lumen of implant 52, in accordance with an application of the present invention. The implantation of implant 52 may allow repeated access by medical instruments 70 to maxillary sinus 24. In the application illustrated in FIG. 3, an endoscope 72 is used to examine the sinus cavity. Similarly, medical instruments 70 may be used to aspirate the sinus or to introduce a drug or other substance to the sinus. In some applications of the invention, medical instrument 70 may be used to prepare the maxillary sinus for a sinus lift operation (e.g., by delivery of a drug to the sinus), in order to reduce inflammation (such as inflammation of mucosal lining 36, e.g., the Schneiderian membrane). Alternatively or additionally, medical instrument 70 may be used to treat pain and/or swelling following a sinus lift operation.

Reference is made to FIGS. 4A-E, which illustrate hole-forming member 50, in accordance with five respective applications of the present invention.

Figure 4A:
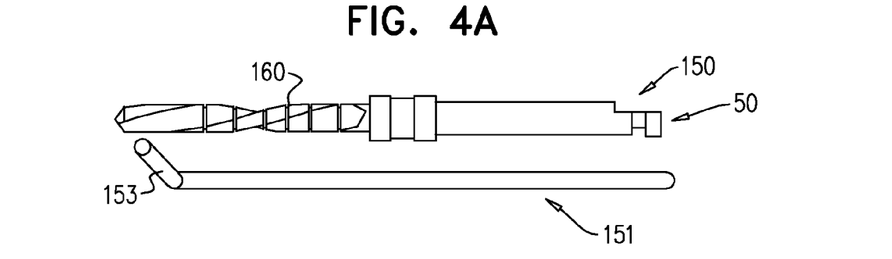
FIGS. 4A-E are schematic illustrations of the hole-forming member used to form a hole in the bone wall of a paranasal sinus, in accordance with respective applications of the present invention.

FIG. 4A illustrates hole-forming member 50, comprising a drill 150. The hole-forming function of drill 150 is imparted, as per a classical drill, by rotation of a drill bit 160. FIG. 4A further illustrates a cooling element 151 for use in conjunction with hole-forming member 50. Cooling element 151 may be used to administer cooling to hole-forming member 50 prior to formation of hole 40. Alternatively or additionally, cooling element 151 may be used to administer cooling to bone wall 32 at the site of hole formation, prior to formation of hole 40. Alternatively or additionally, cooling element 151 is used to administer cooling to hole-forming member 50 and/or bone wall 32 during and/or after formation of hole 40. Cooling element 151 typically utilizes the expansion of a compressed gas to apply its cooling effect. For example, a compressed gas may be applied to drill bit 160 via nozzle 153, whereby expansion of the gas cools the drill bit. Alternatively, cooling element 151 utilizes a cooled liquid (e.g., saline) to apply its cooling effect. Cooling of hole-forming member 50 and/or bone wall 32 is hypothesized to reduce pain and/or the damage caused to tissue in the area of hole formation.

Figure 4B:
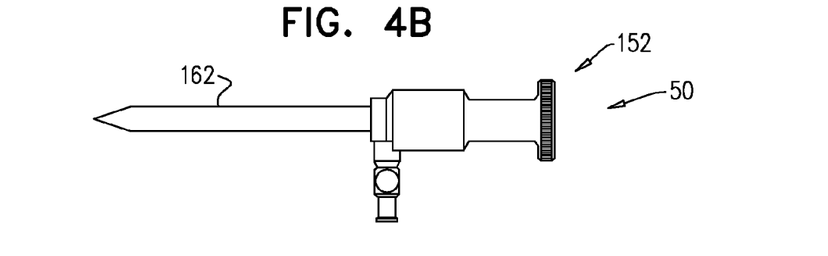

FIG. 4B illustrates hole-forming member 50, comprising a piercing device 152. The hole-forming function of piercing device 152 is imparted by distal movement of a piercing element 162.

Figure 4C:
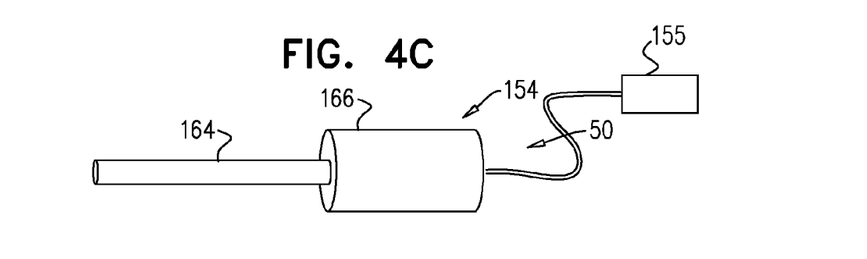

FIG. 4C illustrates hole-forming member 50, comprising an energy applicator 154, typically comprising a control unit 155, a handle 166 and a tip 164. For some applications, energy applicator 154 comprises an ultrasonic drill, for example, an ultrasonic/sonic driller/corer (USDC). The hole-forming function of the ultrasonic drill is imparted by ultrasonic vibration of the tip 164 in contact with bone wall 32. The ultrasonic vibration is typically provided by a piezoelectric actuator in handle 166.

For some applications, energy applicator 154 comprises a radio frequency (RF) electrode. In this example, tip 164 comprises the RF electrode, typically driven by the control unit 155 to apply a current having a frequency and amplitude suitable for forming a hole in bone wall 32. The control unit may also drive the electrode to apply a current having a frequency and amplitude suitable for cauterizing the area of hole-formation. A cauterizing RF electrode may also be employed in combination with other embodiments of hole-forming member 50 (e.g., those described with reference to FIGS. 4A, 4B, 4D and 4E), in order to reduce bleeding during and after formation of hole 40 (see FIGS. 8A-C for an example of such a combination).

Figure 4D:
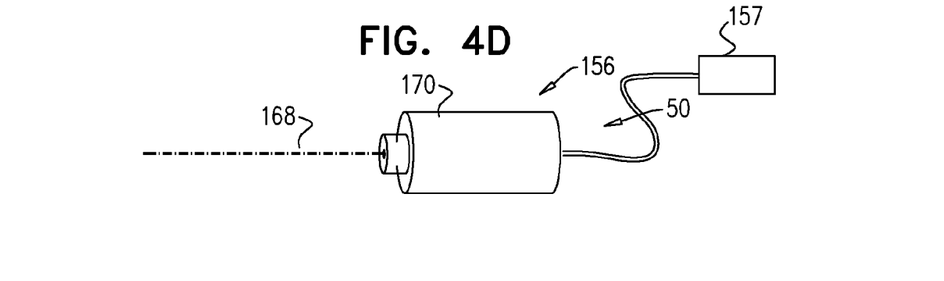

FIG. 4D illustrates hole-forming member 50, comprising a laser cutter 156. A laser 170 generates a laser beam 168 which imparts energy sufficient to form hole 40 in bone wall 32. The laser is controlled by control unit 157.

Figure 4E:
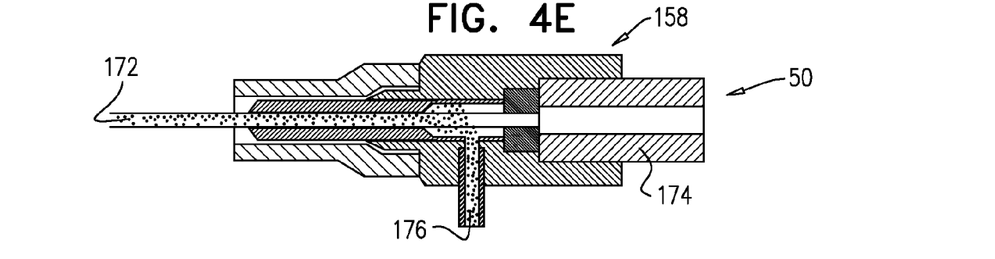

FIG. 4E illustrates hole-forming member 50, comprising a water jet cutter 158. A pump 174 forces water at high pressure through the water jet cutter where it is optionally mixed with an abrasive 176. Abrasive 176 typically comprises particles of a solid substance such as a mineral, a polymer or a frozen aqueous solution (e.g., frozen saline). A water jet 172 is ejected, forming hole 40 in bone wall 32.

Both laser cutter 156 and water jet cutter 158 function by formation of an energetic stream (laser beam 168 and water jet 172, respectively). These applications of the invention may comprise multiple converging streams which focus their energy at a specific distance, reducing the risk of damage to the inside of the sinus due to inadvertent entry of the stream immediately following successful formation of the hole 40. Alternatively, laser cutter 156 generates a straight beam 168, and/or water jet cutter 158 generates a straight water jet 172 (as shown).

Cooling element 151 is illustrated in FIG. 4A in conjunction with drill 150, but may be used in conjunction with numerous embodiments of hole-forming member 50 including, but not limited to, piercing device 152, energy applicator 154, laser cutter 156 and water jet cutter 158, as well as other hole-forming members.

Reference is now made to FIGS. 5A-D, which illustrate four versions of implant 52, in accordance with respective applications of the present invention. Each version of implant 52 is shaped to define a lumen 100. Each version features a shoulder 102 which, being wider than more distal regions of implant 52, inhibits implant 52 from entering the sinus cavity entirely. Alternatively, versions of implant 52 may not include shoulder 102. Each version of implant 52 illustrated in this figure has a fastener which, together with, or independently from, shoulder 102, fastens implant 52 in hole 40 formed in bone wall 32. Optionally, implant 52 may comprise a biodegradable material such as (but not limited to) polyglycolide (PGA), polylactide (PLA) or another biodegradable material known in the art. Implant 52 may be entirely biodegradable.

Figure 5A:
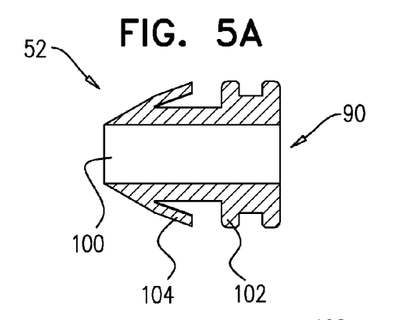
FIGS. 5A-E are schematic illustrations of a paranasal sinus implant, in accordance with respective applications of the present invention.

FIG. 5A is a schematic illustration of implant 52, embodied as a push-in implant 90. The fastener of this implant is one or more extendable members, such as wings 104. Due to their flexibility and angle, wings 104 are able to flex inwardly and pass through the formed hole 40 in bone wall 32 when implant 52 is inserted through the bone wall. Wings 104 return to their original position once on the sinus side of bone wall 32, fastening implant 52 in place.

Figure 5B:
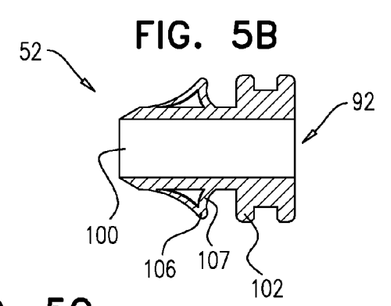

FIG. 5B is a schematic illustration of implant 52, embodied as a push-in implant 92. Implant 92 comprises a fastener comprising one or more extendable members, such as wings 106. Wings 106 are similar to wings 104 of implant 90, but are coupled to the body of the implant by a support 107 at an additional longitudinal site along the implant, and provide greater contact with the sinus-side of bone wall 32, compared to contact provided by wings 104 of implant 90.

Figure 5C:
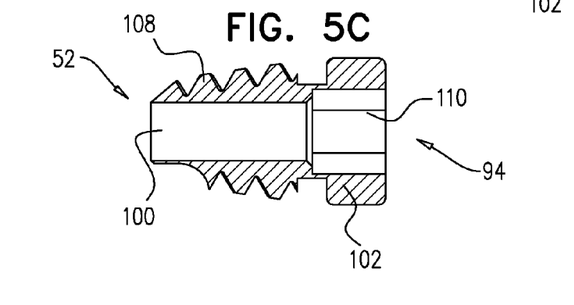

FIG. 5C is a schematic illustration of implant 52, embodied as a screw-in implant 94. The fastener of this implant is a screw thread 108. Following positioning of implant 94 at hole 40, the implant is fastened into the hole by rotation, as per a classical screw. For some applications, this rotation may be imparted by the hole-forming member 50. In applications in which hole-forming member 50 forms hole 40 by rotation, implant 94 may be fastened using the same rotational force that is used to form the opening in bone wall 32. In these applications of the invention, implant 94 may be reversibly coupled to hole-forming member 50 in a manner that prevents independent rotation (e.g., using a hex socket). For example, screw-in implant 94 may be reversibly coupled to drill 150, such that, after formation of hole 40, continued rotation of drill 150 fastens implant 94 into the hole. Alternatively or additionally, rotational force may be applied separately, after hole 40 has been formed.

As described hereinabove, in some applications of the invention, implant 52 (or screw-in implant 94) is self-tapping, comprising a self-tapping screw-thread. In these applications of the invention, no independent hole-forming member is required. Rather, implant 52 is pushed against bone wall 32 and rotated such that it cuts into, and becomes implanted in, the bone wall.

Figure 5D:
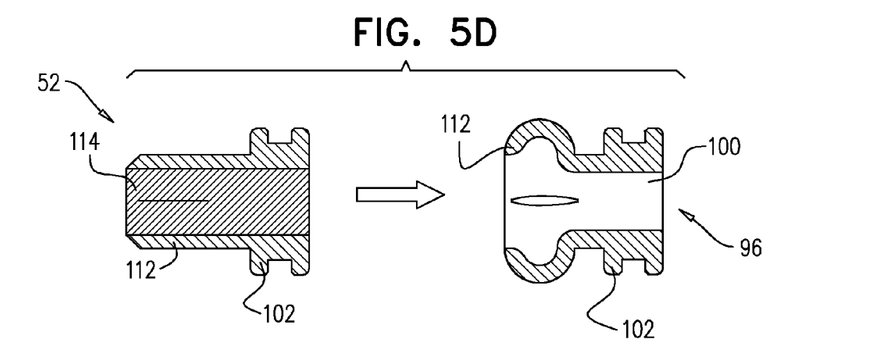

Reference is made to FIG. 5D, which illustrates implant 52, embodied as a rivet implant 96. Rivet implant 96 has a configuration similar to a blind rivet. The fastener of this version is buck-tail 112. The implant is supplied in a restrained first configuration (left drawing) and is maintained in this configuration by a restraint, such as splint 114. Upon removal of splint 114, buck-tail 112 moves to a relaxed second configuration (right drawing). The relaxed configuration of buck-tail 112 is wider than the hole 40 formed in bone wall 32 and therefore fastens the implant in place.

Figure 5E:
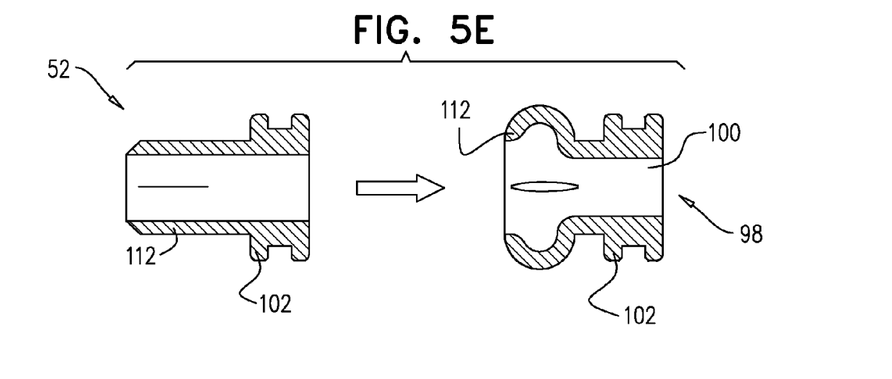

Reference is now made to FIG. 5E, which illustrates a rivet implant 98, according to an application of the invention. Rivet implant 98 is similar to rivet implant 96 but does not comprise a restraint; rather the buck-tail is distorted from a first configuration to a second configuration by a force applied by an applicator. FIG. 6 illustrates such an applicator, according to an application of the invention.

Figure 6A:
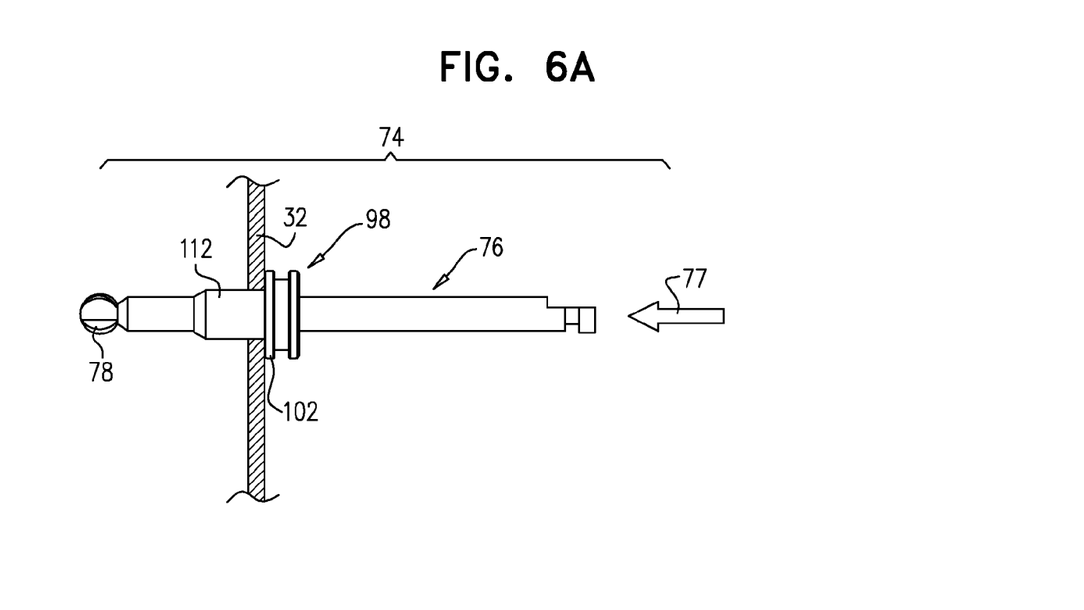
FIGS. 6A-B are schematic illustrations of two sequential steps in the implantation of a rivet implant, in accordance with an application of the invention.
Figure 6B:
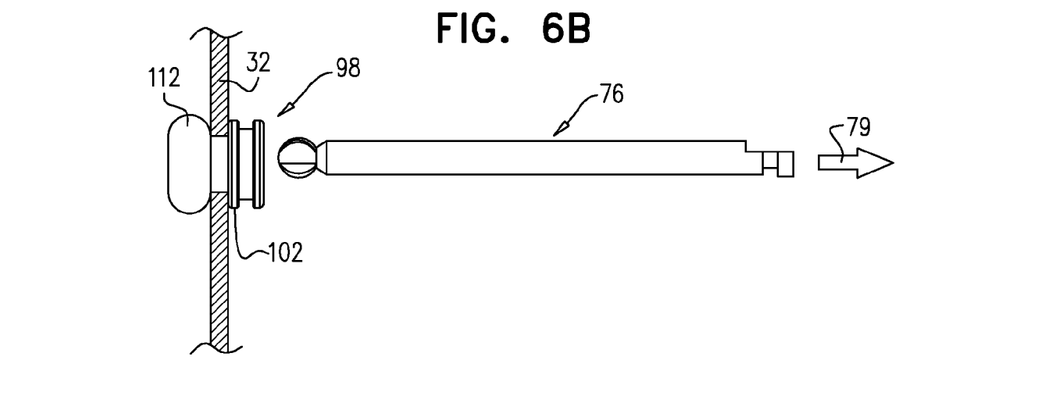

FIGS. 6A-B are schematic illustrations, showing two sequential steps in the implantation of rivet implant 98, in accordance with an application of the invention. Reference is made to FIG. 6A. Rivet assembly 74, comprising an applicator 76 and rivet implant 98, is inserted into hole 40 in the direction of arrow 77, until a shoulder 102 of the rivet implant abuts the proximal surface of bone wall 32. As described with reference to FIG. 5E, rivet implant 98 is configured so as to act as a blind rivet. Correspondingly, applicator 76 is configured so as to act as an appropriate mandrel.

Reference is now made to FIG. 6B. Applicator 76 is withdrawn in the direction of arrow 79, driving a mandrel head 78 into and then out of buck-tail 112. Mandrel head 78 deforms buck-tail 112 of rivet implant 98 into a configuration that fastens the implant in place.

Although FIGS. 6A-B illustrate rivet implant 98 being implanted in a hole in bone wall 32 of a paranasal sinus, rivet implant 98 may be implanted in a hole in other tissues (e.g., an anatomical wall, such as a wall of a hollow organ, for example, a bone wall) of a subject. Alternatively or additionally, rivet implant 98 is solid, i.e., not shaped to define a lumen.

Figure 7:
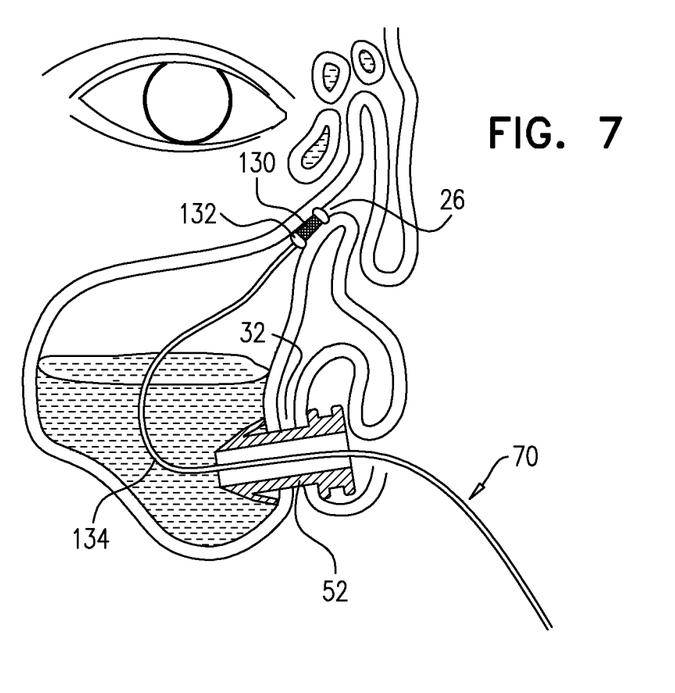
FIG. 7 is a schematic illustration of the implantation of an expandable stent in a sinus ostium, in accordance with an application of the invention.

Reference is made to FIG. 7, which is a schematic illustration of an application of the invention. After implantation of implant 52, a medical instrument 70, which in this application comprises a balloon catheter 134, is used to implant an expandable stent 130 in a natural sinus ostium 26. In its initial form, balloon 132 is disposed within the lumen of stent 130 in a deflated form. Catheter 134 is used to insert stent 130 and balloon 132 through hole 40, through sinus 24 and finally into ostium 26. The balloon 132 is then inflated, expanding stent 130 and opening the ostium. Balloon 132 is then deflated and removed using balloon catheter 134. Due to its configuration, stent 130 remains expanded, supporting ostium 26 in an open configuration. Alternatively, expandable stent 130 may be delivered to ostium 26 in a contracted form and configured to expand passively when a force contracting the stent is removed. For example, stent 130 may be delivered within a sheath. Upon removal of the sheath, the stent expands, supporting ostium 26 in an open configuration.

Such implantation of stent 130 in a sinus ostium may also be performed without passage through a formed hole in a sinus wall. For example, stent 130 could be advanced through the nasal cavity, between inferior turbinate 30 and middle turbinate 28 and into ostium 26. Implantation of stent 130 may be assisted by the use of a guidewire and/or an endoscope. Stent 130 may comprise a biodegradable material such as (but not limited to) polyglycolide (PGA), polylactide (PLA) or another biodegradable material known in the art. Implant 130 may be entirely biodegradable.

Figure 8A:
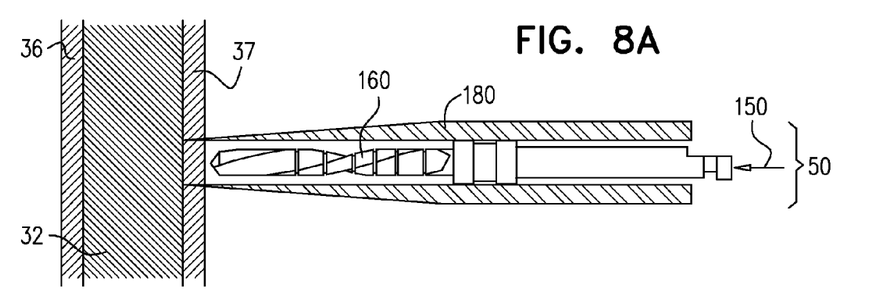
FIGS. 8A-C are schematic illustrations of sequential steps in the formation of a hole in the wall of the paranasal sinus with a cauterizing hole-forming member, in accordance with an application of the invention.
Figure 8B:
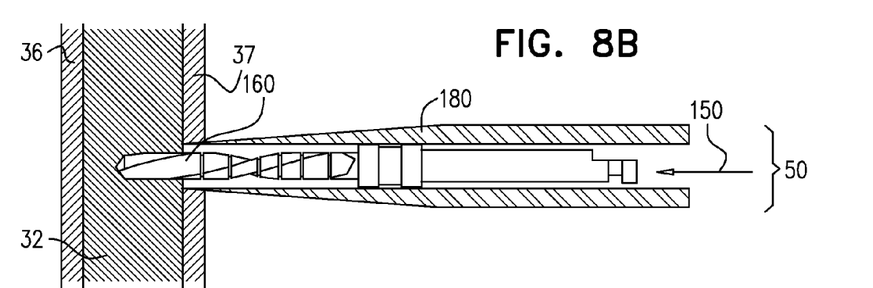
Figure 8C:
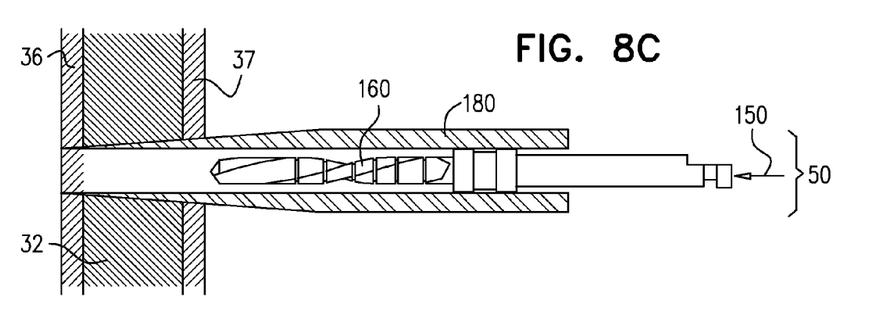

Reference is made to FIGS. 8A-C, which are schematic illustrations of a hole being formed in bone wall 32, in accordance with an application of the invention. In this application of the invention, hole-forming member 50 comprises one or more RF electrodes 180 and drill bit 160. As described hereinabove, hole-forming member 50 is used to create hole 40 in bone wall 32 that divides nasal cavity 38 from maxillary sinus 24. In this application of the invention, electrodes 180 are configured to penetrate soft tissue 37 of the nasal cavity and mucosal lining 36 of the sinus, and to cauterize these tissues.

Reference is now made to FIG. 8A. Hole-forming member 50 is advanced toward bone wall 32. The distal tips of electrodes 180 are disposed distal to the distal tip of drill bit 160. Electrodes 180 penetrate and cauterize soft tissue 37.

Reference is now made to FIG. 8B. Drill bit 160 is extended distally through the hole formed in soft tissue 37, and is rotated in order to drill through bone wall 32.

Reference is now made to FIG. 8C. Electrodes 180 are extended distally through the hole formed in bone wall 32, and penetrate and cauterize mucosal lining 36. FIG. 8C shows drill bit 160 as retracted prior to this extension of electrodes 180. Alternatively, electrodes 180 may slide over drill bit 160, drill bit 160 remaining in the hole in bone wall 32 until after mucosal lining 36 has been penetrated.

It is noted that the cauterization described with reference to FIG. 8A may be performed without the step of cauterization described with reference to FIG. 8C, and that the cauterization described with reference to FIG. 8C may be performed without the step of cauterization described with reference to FIG. 8A.

In an alternative application of the invention, hole-forming member 50 does not comprise RF electrodes 180; rather, RF electrodes 180 are coupled to hole-forming member 50, and are configured to cauterize. Typically, RF electrodes 180 are controlled by a control unit (such as control unit 155, described with reference to FIG. 4C). In this application of the invention, hole-forming member 50 (e.g., drill bit 160) penetrates soft tissue 37 and mucosal lining 36, in addition to bone wall 32. Electrodes 180 cauterize soft tissue 37 and mucosal lining 36 following the penetration of these tissues by the hole-forming member. Typically, RF electrodes 180 are fixed in position with respect to drill bit 160, such that the tips of electrodes 180 are slightly proximal to the tip of drill bit 160 (e.g., less than 3 mm from the tip). Alternatively, RF electrodes 180 may be slidable with respect to hole-forming member 50.

It will be appreciated by persons skilled in the art that the present invention is not limited to what has been particularly shown and described hereinabove. Rather, the scope of the present invention includes both combinations and subcombinations of the various features described hereinabove, as well as variations and modifications thereof that are not in the prior art, which would occur to persons skilled in the art upon reading the foregoing description.

The invention claimed is:

1. Paranasal sinus apparatus comprising:
   an implant, shaped to define a lumen, and securable in a wall of a paranasal sinus of a subject such that a first end of the lumen is in the paranasal sinus and a second end of the lumen is out of the sinus;
   a catheter, slidable through the lumen of the implant;
   a balloon, couplable to a distal portion of the catheter; and
   an expandable stent, slidable through the lumen of the implant while the implant remains secured in the wall of the paranasal sinus, shaped to define a lumen, and configured such that it may be expanded from a first shape to an expanded shape by an applied force,
   the balloon being inflatable via the catheter, and disposable within the lumen of the expandable stent such that inflation of the balloon expands the expandable stent, and
   the expandable stent being maintainable in the expanded shape when the balloon is deflated.

2. The apparatus according to claim 1, wherein the balloon is coupled to the distal portion of the catheter.

3. The apparatus according to claim 1, wherein the stent comprises a biodegradable material.

4. The apparatus according to claim 1, wherein the apparatus further comprises a guidewire, and wherein the catheter is advanceable over the guidewire.

5. The apparatus according to claim 1, wherein the implant comprises a fastener shaped to secure the implant in the wall.

6. A method for treating a paranasal sinus of a subject, the method comprising:
   forming an artificial hole in a wall of the sinus;
   securing, in the artificial hole, an implant shaped to define a lumen, such that a first end of the lumen is in the paranasal sinus and a second end of the lumen is out of the sinus; and
   subsequently, via the lumen of the implant, and while the implant remains secured in the artificial hole:
      inserting an expandable stent into the sinus, and from inside of the sinus, placing the stent into a natural ostium of the sinus;
      sliding, into the sinus, a catheter and a balloon coupled to a distal portion of the catheter;

expanding the stent from a first shape to an expanded shape by applying a force to the stent by inflating the balloon via the catheter while the balloon is inside a lumen of the stent; and deflating the balloon such that the stent is maintained in the expanded shape.

7. The method according to claim 6, further comprising, after implanting the implant and before placing the stent into the natural ostium, inserting a medical instrument via the lumen of the implant and into the paranasal sinus, and using the medical instrument to open the natural ostium.

8. The method according to claim 6, further comprising cauterizing tissue in an area of the artificial hole.

9. Paranasal sinus apparatus comprising:

an implant, implantable in a wall of a paranasal sinus of a subject, comprising a fastener shaped to secure the implant in the wall, the implant being shaped to define a lumen;

a catheter, slidable through the lumen of the implant;

a balloon, couplable to a distal portion of the catheter; and an expandable stent, slidable through the lumen of the implant while the implant remains secured in the wall of the paranasal sinus, shaped to define a lumen, and configured such that it may be expanded from a first shape to an expanded shape by an applied force, the balloon being inflatable via the catheter, and disposable within the lumen of the expandable stent such that inflation of the balloon expands the expandable stent, and the expandable stent being maintainable in the expanded shape when the balloon is deflated.

* * * * *